United States Patent [19]

Chang

[11] Patent Number: 4,507,555

[45] Date of Patent: Mar. 26, 1985

[54] PARALLEL MASS SPECTROMETER

[76] Inventor: Chang Chang, 3065 Maginn Dr., Xenia, Ohio 45385

[21] Appl. No.: 472,161

[22] Filed: Mar. 4, 1983

[51] Int. Cl.³ .............................................. B01D 59/44
[52] U.S. Cl. .................................... 250/281; 250/283; 250/282
[58] Field of Search ............... 250/281, 282, 283, 288, 250/292, 300

[56] References Cited

U.S. PATENT DOCUMENTS

| 3,307,033 | 2/1967 | Vestal | 250/281 |
| 3,479,504 | 11/1969 | Hull | 250/300 |
| 3,510,647 | 5/1970 | Wood | 250/281 |
| 4,209,697 | 6/1980 | Renner et al. | 250/282 |
| 4,266,127 | 5/1981 | Chang | 250/288 |
| 4,283,626 | 8/1981 | Siegel | 250/292 |
| 4,377,745 | 3/1983 | Chang | 250/292 |

OTHER PUBLICATIONS

"A 15-cm Radius Mass Spectrometer Which Simultaneously Collects Positive and Negative Ions" by Harry J. Svec and Gerald D. Flesch, Journal of Mass Spectrometry and Ion Physics, 1 (1968), pp. 41-52.

"Special Techniques in the Combination of Gas Chromatography and Mass Spectrometry", by D. Henneberg, U. Henrichs and G. Schomburg, Journal of Chromatography, 112 (1975), pp. 343-352.

"Design, Implementation, and Performance of a High Resolution Gas Chromatography/High Resolution Mass Spectrometry/Real-Time Computer System for the Analysis of Complex Organic Mixtures", by J. Meili, F. C. Walls, R. McPherron and A. L. Burlingame, Journal of Chromatographic Science, 17 (1979), pp. 29-42.

Primary Examiner—Alfred E. Smith
Assistant Examiner—R. Hanig
Attorney, Agent, or Firm—Jacox & Meckstroth

[57] ABSTRACT

A parallel mass spectrometer, which consists of two or more sets of ion extraction means, mass resolution devices and ion detectors connected in parallel, is interfaced with a separation device, such as a gas chromatograph, for sample analysis. The formed sample ions are simultaneously and separately directed into first and second mass resolution devices. The first mass resolution device is operated under either total ion current or select ions monitoring mode with its detection system constantly monitoring the appearance of the chromatographic peaks. The second mass resolution device is operated under a mass scanning mode, but a mass scan operation is initiated only when a chromatographic peak occurs. Alternatively, a mass scan operation can be arranged such that only the raw mass scan data obtained in synchronization with the appearance of the chromatographic peak are acquired or processed. This allows sample qualitative and quantitative analysis to be achieved simultaneously without compromise on the performance of either the chromatograph or mass spectrometer.

42 Claims, 3 Drawing Figures

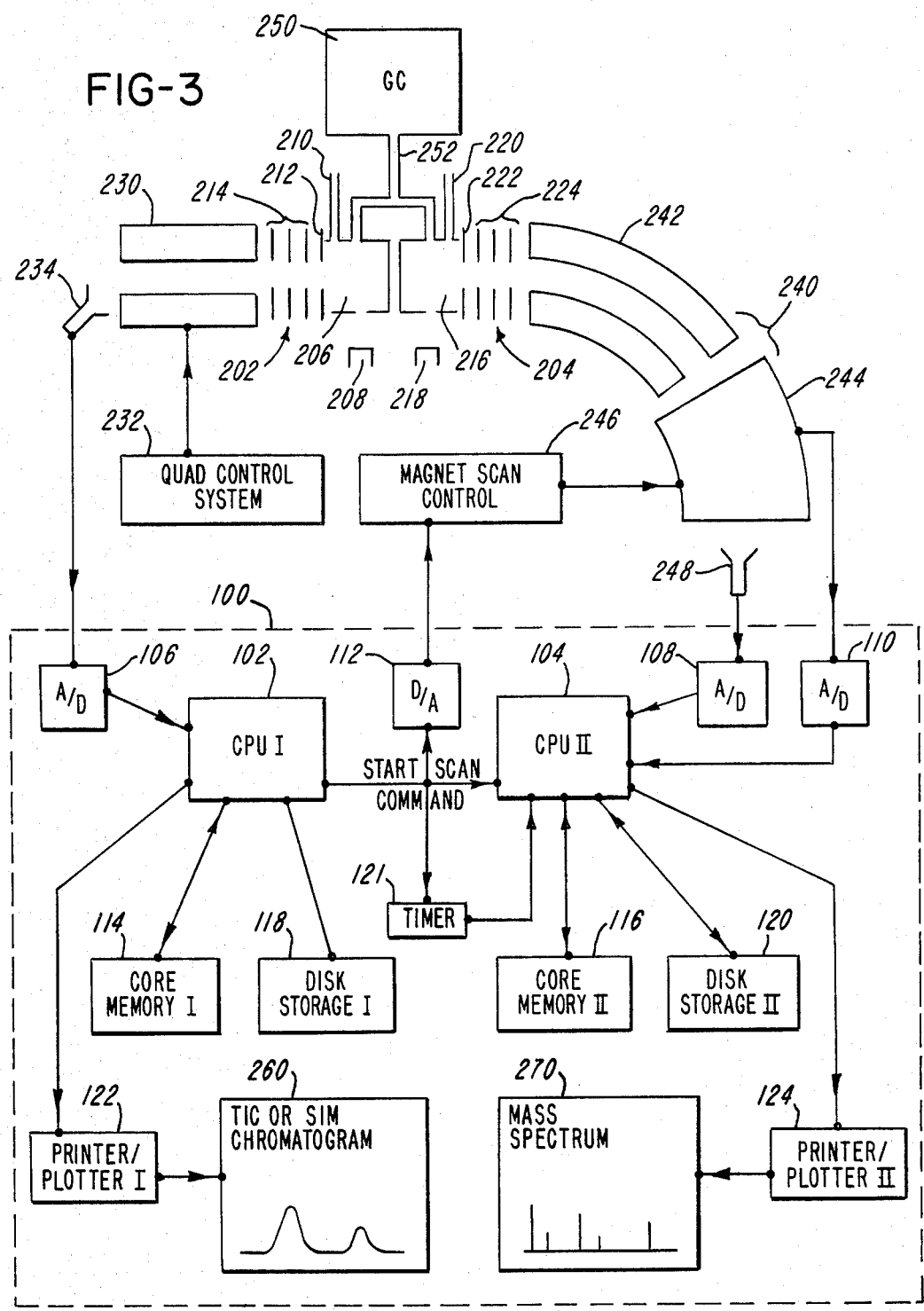

PARALLEL MASS SPECTROMETER

BACKGROUND OF THE INVENTION

The parallel mass spectrometer (PMS) is defined as a mass spectrometer (MS) which consists of two or more sets of ion extraction means, mass resolution devices (quadrupole mass filters, magnetic sections, etc.) and ion detectors (electron multiplier, etc.) connected in parallel. It permits two or more ion beams characteristic of the introduced sample to be extracted, mass resolved, and detected simultaneously. The PMS differs from the commonly known tandem mass spectrometer in which two or more mass resolution devices are connected in tandem and in which only one beam is formed and only one detector is normally employed. The PMS acts virtually in the same manner as two independent mass spectrometers, positioned side by side, but with considerable saving in the construction cost and with more efficient utilization of the sample materials and the obtained data.

The PMS is known to exist in the prior art in various forms. Svec and Flesch (J. Mass Spect. Ion Phys., 1, 41, 1968) first reportedly constructed a PMS consisting of two magnetic sectors for simultaneously analyzing positive and negative ions extracted from an electron impact ionization (EI) ion source. Another PMS was reported (D. Henneberg, U. Henrichs and G. Schomburg, J. Chromatography, 122, 343, 1975) in which a quadrupole mass analyzer with its own ion source and detector was added to a gas chromatograph (GC)—magnetic sector mass spectrometer system. In U.S. Pat. No. 4,266,127, a new type of PMS consisting of two quadrupole mass analyzers for simultaneous positive ion negative ion chemical ionization (SPINICI) operation was described.

One obvious advantage of the PMS over the conventional single mass spectrometer is that in the PMS the two detected sample ion beams can be of different charge polarities and/or derived from different ion formation mechanisms such as EI, CI, photoionization, neutral or charged particle bombardment, etc. The information obtained from these two ion beams are often complementary to each other and greatly facilitate the analysis of the sample in question.

When interfaced with a sample separation device, such as gas chromatograph (GC) or liquid chromatograph (LC), the PMS can also provide a significant advantage over the conventional single mass spectrometers. For example, in a PMS the first mass resolution device can be operated in a select ion monitoring (SIM) mode. This is achieved by tuning the first mass resolution device to one ion (single ion monitoring) or several ions (multiple ion monitoring) of interest. The obtained SIM trace (SIM chromatogram or mass chromatogram) is far superior over the reconstructed mass chromatogram trace (described below) in terms of the chromatographic resolution and detection sensitivity (by a factor of 100 or more). In the meantime, the second mass resolution device can be operated in a repetitive mass scanning mode which yields mass spectra for the qualitative identification of each chromatographic peak.

Alternatively, the first mass resolution device can be operated in a total ion current (TIC) detection mode. This is normally achieved through rapid mass scanning with signal integration. The obtained TIC trace (TIC chromatogram) is also much better than the reconstructed TIC trace (Described below) in terms of the chromatographic resolution and retention index accuracy. Furthermore, if the first mass resolution device is a quadrupole type which is capable of operation in a RF-only mode, the resultant TIC trace is of even better chromatographic resolution and detection sensitivity (by a factor of 100 or more) than any other type of TIC trace.

In conventional single mass spectrometers, various forms of ion beam monitors are also known to exist which allow a fraction of the extracted ion beam to be detected independent of the operation of the mass resolution device. However, these types of ion beam monitors have been found to be unacceptable for quantitative GC-MS analysis, because the obtained ion signal generally consists of a high level noise, resulting from species, such as the GC carrier gas, CI reagent gas, GC column bleed, and instrument background, commonly presented in a GC-MS environment. For this reason, these ion beam monitors are rarely used in a GC-MC experiment, except for tuning the mass spectrometer. On the contrary, the TIC trace obtained with mass resolution device filtration, such as in a PMS system is largely free from such noise, because the mass resolution device can be properly programmed to screen out most unwanted noise.

However, in spite of the above-described advantages, the PMS as operated in the SIM (or TIC)—repetitive mass spectra acquisition mode offers little improvement over the conventional single mass spectrometer in obtaining the mass spectra data.

The repetitive mass spectra acquisition operation is widely adopted in most modern GC-MS-computer systems. However, there are several fundamental problems associated with the repetitive mass spectra acquisition operation which are generally understood but can not be avoided because of lack of suitable solutions.

One of the major reasons for employing the repetitive mass spectra acquisition operation is that during a GC-MS experiment one does not know when a GC component will enter the mass spectrometer and needs to be analyzed by obtaining a mass spectrum data. The only solution available then is to perform the repetitive mass scan and blindly acquire and process all mass scan data at rapid rates during the entire GC run, so that all GC components flowing from the GC column and entering the mass spectrometer will be analyzed, regardless of the appearance time of the GC components. However, since only the mass spectra recorded in coincidence with the appearance of the GC peaks are of value, all of the other spectra recorded are simply a waste of computer time and memory storage, except for a few spectra which are utilized for background subtraction.

In a typical repetitive mass spectra acquisition operation, the mass scanning rate is adjusted so that there are at least ten complete mass scans across each GC peak, in order to minimize the spectrum distortion, resulting from the rapid change of the sample concentration in the ion source, and to ensure that a good mass spectrum can be recorded at the GC peak top region. For a GC peak width of 10 seconds the minimum acceptable mass scanning rate will be one mass scan cycle per second. This means that during an one-hour period of GC run, as many as 3600 ($1 \times 60 \times 60$) mass spectra have to be acquired, processed and stored in a computer system. An extremely large computer system is therefore required. This is especially true for a high resolution GC—high resolution MS system. The demand on the interfaced computer capability is therefore enormous and rarely possible.

One common treatment of the acquired repetitive mass scan data is that of obtaining a reconstructed TIC trace by summing all ion currents (in digital form) within each scan and plotting this sum vs. the scan number. Alternatively, one or more reconstructed mass chromatograph traces can be obtained by plotting the intensity of one or more ions of particular m/e values in each scan data vs. the scan number. These reconstructed TIC or mass chromatographs traces generally resemble a normal gas chromatograph trace recorded continuously with a GC detector, such as a flame ionization detector or a mass spectrometer operated in the real TIC or SIM mode. However, there is one significant difference in that there is only one date point for each mass scan in the reconstructed TIC or mass chromatograph trace. The achievable chromatographic resolution in this trace largely depends on the number of mass scan cycles which can be performed within each GC peak retention time. In the above example, for a GC peak width of 10 seconds and a mass scan rate at one mass scan cycle per second, a total of only 10 data points can be recorded across each GC peak as represented by the reconstructed TIC or mass chromatograph trace. The poor chromatographic resolution resulting from this limited number of data points severely compromised the GC performance and makes it very difficult to obtain an accurate peak retention index, which is the most important parameter for peak identification in gas chromatography.

It is clear from the above discussion that in order to prevent excessive deterioration in the chromatographic resolution, the mass scan rate for a repetitive mass spectra acquisition GC-MS analysis should be adjusted as rapid as practical. Unfortunately, a rapid mass scan rate brings with it the problem of deterioration of the mass spectrum detection sensitivity and spectra quality. Both these two factors, to a large extent, depend on the duration of each mass scan period, in which the longer the scan period, the better the detection sensitivity and spectra quality. The contradicting nature of the GC resolution and MS spectra quality and sensitivity requirements makes it practically impossible to achieve a GC-MS analysis without compromise in the performance of either GC or MS or both in a repetitive mass spectra acquisition operation.

The compromise in GC and/or MS performance becomes even more severe in the case of a high resolution GC-high resolution MS system operated under repetitive mass spectra acquisition mode. Because of the restraint on the MS spectra quality requirement, the maximum achievable high resolution mass scan cycle is only in the order of 5-10 seconds. This time period is far inadequate for most high resolution (capillary) columns which normally yield peak width of 10-20 seconds. The chromatographic resolution of the reconstructed TIC or mass chromatograph trace is of a quality too poor to be of significant analytical value. To circumvent this problem, most modern high resolution mass spectrometers are simply operated under low mass resolution when interfaced with a high resolution GC column. This is indeed a severe loss to a mass spectrometer originally designed for high mass resolution and which cost several times that of a low resolution mass spectrometer.

With the advance of GC separation technology, the average GC peak width becomes narrower and narrower. It is not uncommon that in some glass capillary GC columns the resolved sample component has a peak width of only 1-2 seconds. This type of high performance GC columns is generally considered incompatible with a conventional GC-MS system operated under a repetitive mass spectra acquisition mode. In order to achieve minimum acceptable chromatographic resolution for this narrow peak, the repetitive mass scan rate must be set at 5-10 mass scan cycles per second, which is practically impossible, even for most low resolution mass spectrometers having a maximum useful scan rate of only 1-2 mass scan cycles per second. As a result, GC columns of lower quality must be used. These usually require longer operation time and thus suffer from lower sample analysis throughput.

As mentioned previously, in a GC-MS analysis, the mass spectra recorded during the repetitive mass scan operation are generally distorted as a result of the rapid change of the sample concentration within the ion source of the mass spectrometer. This problem is generally ignored, because there is no simple way to correct for this distortion. Obviously, this problem makes it difficult to compare the obtained spectra with reference spectra for the unknown compound identification.

It is not unusual that in the GC-MS analysis there may be a complex sample which may consist of hundreds of components but in which only a few of the components are of interest for analysis. Specific analysis of these few components is not possible with a repetitive mass spectra acquisition operation. Such an operation is a non-discriminatory analysis method, which will faithfully acquire, process and store the spectra of all components, regardless of their analysis needs. The large volume of unwanted spectra not only wastes the precious computer time and memory storage, but also complicates the final spectra analysis.

SUMMARY OF THE PRESENT INVENTION

The present invention is based upon the realization that in a GC-PMS system the detailed chromatographic information in the form of real time SIM or TIC trace (as opposed to the reconstructed SIM or TIC) can be made available. Therefore, the mass spectra data are required only for one purpose of GC peak identification. This means that the reconstruction of SIM or TIC based on mass spectra data is no longer needed. Furthermore, it is realized that the obtained SIM or TIC trace does contain the information regarding the appearance time of the chromatograph peak, and if this information can be properly utilized, it is possible to initialize a mass scan only during the appearance of each GC peak or acquire or process only the raw mass scan data obtained in synchronization with the appearance of the GC peak. Under this "SIM (or TIC)—synchronized mass spectrum operation only one mass spectrum is acquired and needed for each GC peak for the purpose of GC peak identification.

In the novel operation method of this invention, the number of mass spectra to be acquired, processed and stored can be 2-3 orders of magnitude less than that required in the conventional repetitive mass spectra acquisition operation. This greatly reduces the load on the computer time and storage and also reduces the number of spectra to be analyzed.

With the application of the SIM (or TIC)—synchronized mass spectrum operation in a GC-PMS system, neither the performance of GC or MS will need to be compromised. Since each mass scan can be conducted at a rate much lower (by 5 to 10 times) than that of a repetitive mass spectra acquisition operation, the obtained mass spectra are of much better quality and higher detection sensitivity (up to 5 to 10 times more sensitive).

As a result of the much relaxed mass scan speed requirement in the SIM (or TIC)—synchronized mass spectrum operation, the operation of high resolution GC—high resolution MS no longer presents a problem. For the same reason even the most advanced high resolution GC column with average peak width of 1-2 seconds can be incorporated in a GC-PMS system. Better GC separation and higher sample analysis throughput can therefore be realized.

In SIM (or TIC)—synchronized mass spectrum operation there is a direct correspondence between the detected GC peak and the mass spectrum for the very same peak. The identification of the GC peak through the mass spectrum analysis is straightforward without ambiguity. Furthermore, this direct correspondence, coupled with the obtained SIM (or TIC) trace which directly provides the sample concentration profile information during each mass scan, enables a simple correction method to be used for correcting the distortion in the recorded mass spectra which result from a rapid change of the sample concentration within the ion source.

A GC-PMS system operation under SIM (or TIC)—synchronized mass spectrum operation also allows specific analysis of a few GC components among a complicated sample mixture to be achieved. With proper selection of the ion (or ions) to be monitored, the SIM becomes an efficient screening tool which allows only the components of interest to appear on the SIM trace and to be identified through the mass scan analysis, while the rest of the components are suppressed and remain undetected. This represents the most efficient utilization of both the computer time and storage as well as the manpower effort in dealing with the simplified chromatographic trace and reduced number of mass spectra.

It is therefore a principal object of this invention to provide a novel automated SIM (or TIC)—synchronized mass spectrum operation method using a parallel mass spectrometer system for achieving all the above-described advantages.

Another object of this invention is to provide a novel parallel mass spectrometer system including a peak sensing means which enables the SIM (or TIC)—synchronized mass spectrum operation to be achieved automatically.

Other objects and advantages of this invention reside in the construction of parts, the combination thereof, the method of production and the mode of operation, as will become more apparent from the following description.

BRIEF DESCRIPTION OF THE DRAWINGS

FIG. 3 is a schematic representation of another mass spectrometer system of this invention.

DESCRIPTION OF THE PREFERRED EMBODIMENT

Figure 1:
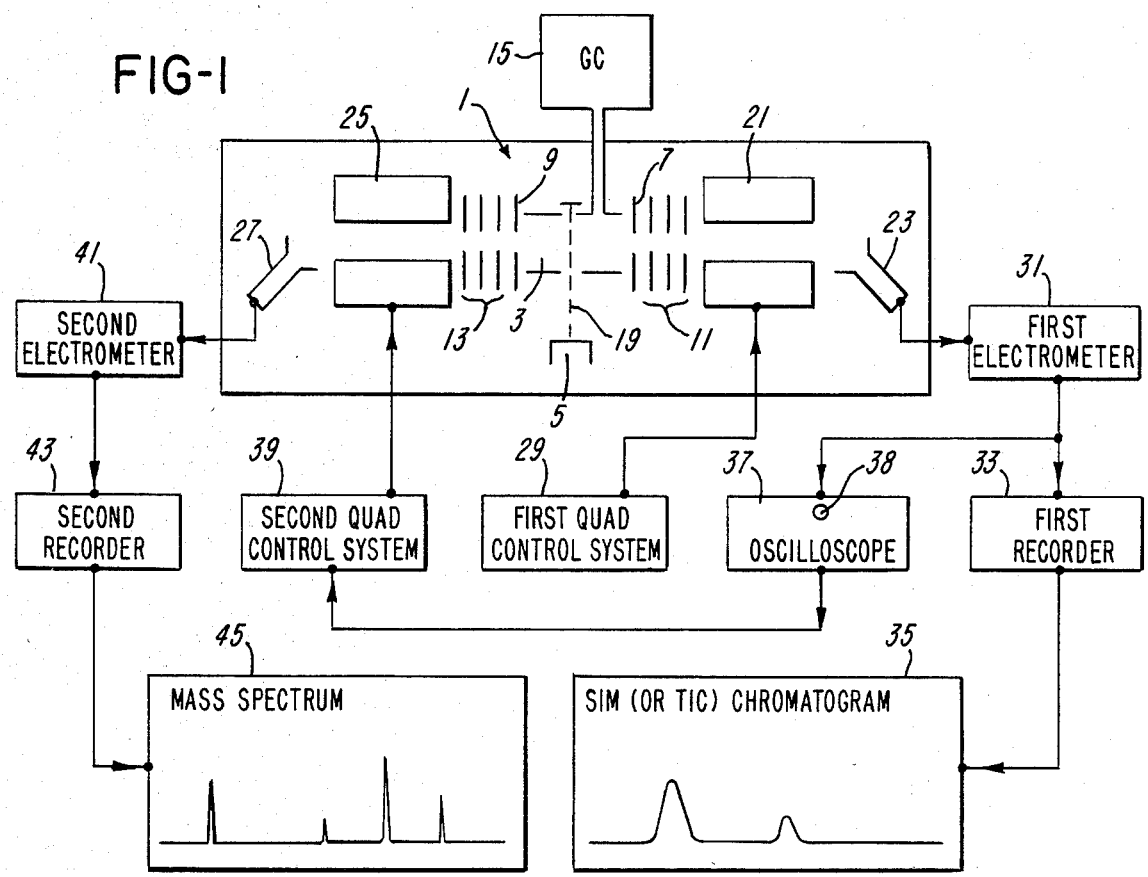
FIG. 1 is a schematic representation of the mass spectrometer system of this invention.

Shown in FIG. 1 is a schematic illustration of a PMS system for SIM (or TIC)—synchronized mass spectrum operation. The mass spectrometer is equipped with an ion source assembly 1 which consists of an ion source 3, a filament 5, a first ion extraction plate 7, a second ion extraction plate 9, a first ion lens assembly 11, and a second ion lens assembly 13. A sample to be analyzed is introduced into the ion source 3 through suitable separation means, such as a gas chromatograph (GC) 15. The introduced sample is then ionized within the ion source 3, in which an electron beam 19 is emitted into the ion source 3 from the filament 5. For simplicity, it is assumed that the ion source assembly 1 is operated in a positive ion electron impact ionization (PIEI) mode. To facilitate the extraction of positive ions from the ion source 3, the ion extraction plates 7 and 9 can be applied with electric potential which is negative with respect to the ion source 3 potential. The ions extracted from the first ion extraction plate 7 are subsequently focused by the first ion lens assembly 11, mass resolved by a first quadrupole mass filter 21, and detected by a first electron multiplier 23. In the meantime, the ions extracted from the second ion extraction plate 9 are focused by the second ion lens assembly 13, mass resolved by a second quadrupole mass filter 25, and detected by a second electron multiplier 27.

The operation of the first quadrupole mass filter 21 is controlled by a first quadrupole control system 29 which is of conventional design. Before the analysis operation this system can be adjusted such that the first quadrupole mass filter 21 is tuned to ions of a specific ion-mass-to-charge-ratio (m/e) of interest (single ion monitoring). For example, if only aromatic components in the sample mixture are to be analyzed the ions with its m/e equal to 91 (ion $C_7H_7^+$) can be monitored because ions of this m/e value are generally found only in the mass spectra of most aromatic compounds and absent in most other spectra. The obtained chromatogram will consist of aromatic component peaks only while all other components are excluded.

Alternatively, the first quadrupole control system 29 can also be adjusted for a different type of select ion monitoring mode operation by monitoring several ions of different m/e values sequentially (multiple ion monitoring) and rapidly.

All collected ion currents are effectively integrated by a first electrometer 31, yielding a chromatogram representing the sum of all monitored ions. For example, in the analysis of a complex mixture for both chlorine-containing and bromine-containing compounds the quadrupole control system 29 can be adjusted for multiple ion monitoring operation by alternately detecting the $Cl^-$ and $Br^-$ ions (at m/e=35 and 79, respectively). In this case the obtained chromatogram will consist of chlorine-containing and/or bromine-containing compound peaks only while all other components are excluded.

On the other hand, if all components flowing from the GC column are to be analyzed the first quadrupole control system 29 can be set to scan rapidly over a mass range of interest at a rate typically faster than 10 mass scans per second. All collected ion currents will be effectively integrated by the first electrometer 31 which yields a total ion current (TIC) chromatogram.

With the use of quadrupole mass filters such as the first quadrupole mass filter 21, it is known in the prior art that a TIC chromatogram can also be obtained by applying the quadrupole mass filter only with RF voltage, in addition to the quadrupole floating voltage. Under this condition the first quadrupole mass filter 21 serves as a high pass filter which transmits all ions with their m/e values higher than a given value, depending on the settings of the first quadrupole control system 29. The frequency and amplitude of the applied RF voltage can be properly selected such that most unwanted ions, such as those resulting from the GC carrier gas and instrument background gas can be eliminated. The obtained TIC chromatogram is typically one to two orders of magnitude more sensitive than that obtained from rapid mass scan followed by signal integration.

During the GC-MS analysis the signal detected by the first electron multiplier 23 is then integrated, amplified and conditioned by the first electrometer 31. The output of the electrometer 31 is subsequently sent to a first recorder 33 yielding a gas chromatograph trace 35 which is either a SIM or TIC trace, depending on the settings of the first quadrupole control system 29.

Furthermore, the signal output from the first electrometer 31 is also sent to an oscilloscope 37 at its time base/amplifier external input 38. This oscilloscope 37 can be set at a normal triggered mode and thus, in this invention, serves as an automatic GC peak sensor. Whenever the signal output from the first electrometer 31 reaches a preselected trigger voltage level, the oscilloscope 37 senses the onset or appearance of a GC peak and sends out a ramp voltage output. This output is then sent to a second quadrupole control system 39 which is described below.

The second quadrupole control system 39 is also of conventional design and is employed for the operation of second quadrupole mass filter 25. This control system 39 is operated under the sweep mode and thus causes a mass scan of the second quadrupole mass filter 25 whenever a ramp voltage is received from the oscilloscope 37. The detected ion signal at the second electron multiplier 27 during this mass scan is subsequently amplified and conditioned by a second electrometer 41, the output of which then appears at a second recorder 43 as a mass spectrum trace 45.

For the purpose of illustration, a set of parameter values listed as follows can be chosen for the present operation:

| Oscilloscope 37 | |
|---|---|
| External Trigger | level (0.1V) |
| | slope (positive) |
| Output | 0 to 10V ramp voltage in 5 seconds |
| Second Quadrupole Control System 39 | |
| Start mass | m/e = 50 |
| Sweep width | m/e = 500 |

With these settings, whenever the output signal from the first electrometer 31 rises to a threshold level of 0.1 V with positive slope a GC peak is recognized and a 5-sec mass scan from m/e=50 to 550 is conducted by the second quadrupole control system 39 and a mass spectrum is generated.

The above described GC-PMS operation constitutes an automated SIM (or TIC)—synchronized mass spectrum operation. The mass scan operation as well as the acquisition of the mass spectrum are synchronized with the onset or appearance of a GC peak in the SIM or TIC trace 35. No mass scan is conducted when there is no GC peak; and during which the output trace on both recorders 33 and 43 appear as a baseline trace. Obviously the acquisition of the mass spectrum is directly controlled by the oscilloscope 37 which serves as an automatic GC peak sensor.

Since only one mass scan is conducted for each GC peak, the duration of each mass scan is made comparable with the general peak width of the GC peak width. In the above example, a 5-second mass scan is chosen which is created for a general GC peak width of 5–10 seconds. For a narrower GC peak width a faster mass scan is chosen; eg. a 1-second mass scan for a GC peak width of 1–2 seconds, etc. Of course, the mass range of each scan is readily adjustable. This is available in most commercial quadrupole control systems.

Figure 2:
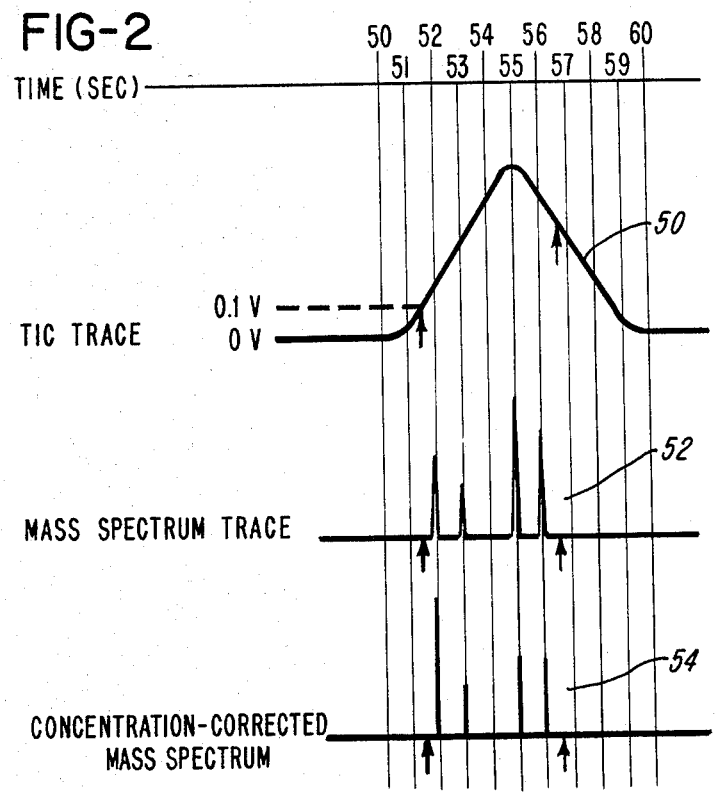
FIG. 2 is a schematic representation of the output traces obtained under the TIC—synchronized mass spectrum operation of this invention.

The above described GC-PMS operation is further clarified by FIG. 2 which shows one section of a TIC trace 50 output from the first electrometer 31 and a mass spectrum 52 output from the second electrometer 41. For simplicity, it is assumed that the GC peak shown in the TIC trace 50 has a peak width of 10 seconds (from time 50 seconds to 60 seconds). As soon as the TIC signal reaches a level of 0.1 V with positive slope (at time 51.5 seconds) a mass scan operation is initiated and the mass spectrum 52 is subsequently recorded which lasts for a period of 5 seconds (from time 51.5 seconds to 56.5 seconds). It is clear that the recording of the mass spectrum 52 is synchronized with the onset or appearance of the TIC peak. The trace 54 is a concentration-corrected mass spectrum which is described below.

It is to be understood that the greatest advantage of the above described SIM (or TIC)—sychronized mass spectrum operation method is its ability to present both quantitative (from TIC or SIM trace) and qualitative (from mass spectrum) information of a sample to be analyzed in such a simple and unambiguous manner. It is assured that each chromatographic peak of significant size is accompanied with a mass spectrum for peak identification. Since both the GC peak and the mass spectrum are recorded at the same time for the same sample component, there is no ambiguity in the correlation between the obtained SIM (or TIC) trace and the mass spectra. The manpower task in analyzing the obtained GC and mass spectra trace are thus greatly simplified.

With the present method, the number of mass spectra to be recorded and stored is also greatly reduced in comparison with the conventional repetitive mass spectra acquisition operation. For computer interfaced GC-MS operation the storage of mass spectra data is often a limiting factor.

In the present operation, since only one mass scan is performed for each GC peak, the duration of each mass scan is extended to a period comparable with the GC peak width. This assures the maximum mass spectra sensitivity, since the longer the scan period, the longer the detection time for each ion mass and the larger the ion current. More accurate ion mass measurement is also achieved with this slower mass scan speed.

In the present method, since normally only one mass scan is required for each GC peak, most advanced GC columns with superior separation efficiency but with narrower peak width and shorter peak retention time are utilized. This naturally leads to better analysis results and larger sample analysis throughput.

The present operation method also provides an unique flexibility in that the sample analysis can be tailored to fit the specific analysis need. For example, the TIC monitoring is a non-discriminating analysis method, therefore, in a TIC—synchronized mass spectrum operation all components in the sample mixture are displayed on the chromatogram, along with the mass spectra of all those components. On the other hand, as discussed in the previous example, if only aromatic components in a sample mixture are to be analyzed a SIM—synchronized mass spectrum operation can be adopted. The mass filter 21 in FIG. 1 can be tuned to the ion mass m/e=91 which thus allows the mass spectra of only the aromatic components to be displayed and analyzed. Similar discrimination is also achieved by the adjustment of the threshold trigger level. For example, referring to FIGS. 1 and 2, an adjustment of the threshold trigger level to 0.2 V allows the mass spectra of only the major chromatographic peaks, with their peak height larger than 0.2 V to be displayed and analyzed.

As discussed previously, one of the major advantages of PMS over the conventional single mass spectrometers is that in the PMS the two detected sample ion beams can be derived from different ion formation mechanism and provide complementary information for the sample analysis. This advantage can also be preserved in the present SIM (or TIC) synchronized mass spectrum operation. For example, in FIG. 1 the ion source assembly 1 can be operated in a chemical ionization (CI) operation mode for the simultaneous formation of positive ions and negative ions, both of which are formed from different ion formation mechanisms as well known in the prior art. The CI reagent gas required for the CI operation can be simply the GC carrier gas introduced from the GC 15 in FIG. 1 along with the sample.

Alternatively, other specific CI reagent gases can also be introduced into the ion source 3 through other suitable means, not shown in FIG. 1, but commonly practiced in prior art. In either case, the first ion extraction plate 7 can be applied with a potential positive with respect to that of the ion source 3, thus favoring the extraction of negative ions. On the other hand, the second ion extraction plate 9 can be applied with a potential negative with respect to that of the ion source 3 thus favoring the extraction of positive ions from the ion source 3. It is known from prior art that many chlorine-containing compounds yield large abundance of $Cl^-$ ion which is excellent for the sample quantitative analysis but poor for compound identification. On the other hand, positive ion CI spectra of these compounds are generally more specific but of lower detection sensitivity. A SIM—synchronized mass spectrum operation with the first quadrupole mass filter 21 tuned to a negative ion (m/e=35), and the second quadrupole mass filter 25 set to positive ion mass scan affords a SIM trace with excellent sensitivity for quantitative analysis and a mass spectrum with high specificity for peak identification.

Furthermore, herein SIM (or TIC)—synchronized mass spectrum operation also allows for correction of the distortion in the recorded mass spectra which result from rapid change of sample concentration within the ion source. This distortion is clearly illustrated in the recorded MS trace 52 shown in FIG. 2. This type of distortion can be easily corrected in the present SIM (or TIC)—synchronized mass spectrum operation because of the availability of two vital data: (1) Exact time correspondence between the mass scan and the onset or appearance of a GC peak; (2) Detailed profile of the sample concentration within the ion source as represented in the real time SIM or TIC trace. A simple correction routine can therefore be devised and executed to correct for this distortion based on the above-given data.

The simplest correction routine is to divide the intensity of each ion in the recorded MS trace by the corresponding height shown in the TIC or SIM trace and followed with proper normalization process. Such a correction procedure will yield a concentration—corrected mass spectrum which is also exemplified by the trace 54 shown in FIG. 2. This correction should enable a more accurate mass spectrum to be obtained for peak identification.

With the teaching of this disclosure, many variations can be made on the design of the PMS system for the performance of SIM (or TIC)—synchronized mass spectrum operation. For example, one of the two quadrupole mass filters 25 and 21 shown in FIG. 1 can be replaced with a magnetic sector type of mass resolution device to facilitate high resolution mass analysis. The peak sensor shown in FIG. 1 is an oscilloscope 37, but other types of peak sensors can also be employed to achieve the same function. One good example is the use of a computer system which can be programmed to achieve the peak sensing function in digital form in a manner far more elaborate than that which can be achieved by the use of the oscilloscope.

For the purpose of illustration, FIG. 3 shows another example of a PMS system for the operation of SIM (or TIC)—synchronized mass spectrum operation. It is emphasized that despite the complexity in this system, the underlying principle of the SIM (or TIC)—synchronized mass spectrum operation method is still basically the same as that illustrated in FIG. 1 and described above.

As seen in FIG. 3, the operation of this PMS system heavily relies on an interfaced computer system 100. The components employed for this computer system 100 include central processing units CPUI 102 and CPUII 104, analog-to-digital converters A/D 106, A/D 108, and A/D 110, digital signal-to-analog signal converting means D/A 112, core memory I 114, core memory II 116, disk storage I 118, disk storage II 120, timer 121, printer/plotter I 122, an printer/plotter II 124. All of these are standard hardware elements commonly employed in many computer systems and need not be further described.

Many software mass scan data acquisition and processing programs commonly exist for mass spectrometer data acquisition and processing and can be adopted for the present computer system 100. Furthermore, a peak sensing software program 128 can also be written and executed by the CPUI 102 for sensing the appearance of a GC peak in real time and sending out a command signal to initiate a synchronized mass scan when a (GC) peak occurs. This peak sensing software program 128 is not shown here but software programs in general for sensing a signal trace and sensing an output signal to indicate the on-set of a peak have been broadly used in chromatography. One common form of such a program computes the slope of the incoming signal and compares it with a pre-assigned threshold level (a digital number). Whenever the slope rises to a level higher than the threshold level a peak is sensed and consequently a command signal is sent out to activate the operation of a hardware component.

Located at the center of the PMS system of FIG. 3 are two ion source assemblies, 202 and 204, placed side by side. The first ion source assembly 202 comprises an ion source 206, a filament 208, CI reagent gas inlet 210, an ion extraction plate 212, and ion lens assembly 214. Similarily, the second ion source assembly 204 consists of an ion source 216, filament 218, CI reagent gas inlet 220, ion extraction plate 222, and ion lens assembly 224.

In FIG. 3 to the left of the first ion source assembly 202 is a quadrupole mass filter 230 which is controlled by a quadrupole mass filter control system 232. An electron multiplier 234 is shown for detecting ions emitted from the quadrupole mass filter 230.

To the right of the second ion source assembly 204 is a double focusing mass resolution device 240 which consists of an electrostatic analyzer (or electric sector) 242 and a magnetic sector 244. A magnet scan control system 246 is used to control the operation of the magnetic sector 244. An electron multiplier 248 detects ions emitted from the magnetic sector 244.

The sample to be analyzed is introduced into the ion sources 206 and 216 from any suitable separation means such as a GC 250 and the inlet tubing 252 as shown in the FIG. 3. The introduced sample is then ionized simultaneously, but separately, within the ion sources 206 and 216. A portion of ions formed within the ion source 206 is extracted and then focused by the ion lens assembly 214, mass resolved by the quadrupole mass filter 230, and detected by the electron multiplier 234. Similarly, a portion of the ions formed within the ion source 216 is extracted and then focused by the ion lens assembly 224, energy resolved by the electric section 242, mass resolved by the magnetic sector 244, and detected by the electron multiplier 248.

One preferable form of the SIM (or TIC)—synchronized mass spectrum operation can be performed by adjusting the quadrupole mass filter 230 in the SIM or TIC operation mode, while the magnetic sector 244 is in the synchronized mass spectrum operation mode. The detected ion signal from the electron multiplier 234, after proper amplification and conditioning, is converted to digital form by the A/D 106, acquired and processed by the CPUI 102, and stored in the core memory I 114 and disk storage I 118. The resultant ion signal vs time profile is then displayed by the printer/plotter I 122, which represents a gas chromatograph trace 260 (either SIM or TIC chromatogram) as seen in FIG. 3. Of course, in a computer system, the chromatogram may be set forth in any other form, different from that shown by the trace 260.

In addition to the above described data acquisition and processing, the CPUI 102 is also executing the peak sensing software program 128 in real time for sensing the appearance of a GC peak in the obtained gas chromatogram. Once a GC peak is sensed, as seen in FIG. 3, the CPUI 102 will send out a start scan command signal. This start scan command signal is subsequently transmitted to the D/A 112 which in turn activates the magnet scan control system 246 and initiates a scan operation of the magnetic sector 244. In the meantime this same signal is transmitted to the CPUI 104 to initiate the execution of a data acquisition routine. As seen in FIG. 3 this start scan command signal is also transmitted to the timer 121 which will be described below.

The element D/A 112 generally refers to a digital-signal-to-analog-signal converting means. One of the most commonly employed hardware elements for such use is a conventional digital-to-analog converter which is capable of converting a digital number into an analog voltage signal with high precision. While this converter is certainly useable for the present application, other converting means with less precision is also adequate since to activate a mass scan of the magnet scan control system 246 usually only comprises means to turn on a switch, push button or relay. This type of control is most efficiently achieved with a transistor-to-transistor logic (TTL) integrated circuit system including chips such as a decoder, flip-flop and buffer. All of these have been widely used for computer control of the operation of hardware such as a mass spectrometer. The D/A 112 may by physically located as a part of the computer system 100 as seen in FIG. 3 or may be a built-in component of the magnet scan control system 246.

Prior to the operation the magnet scan control system 246 can be adjusted to perform one mass scan of the magnetic sector 244 upon the reception of a start scan command through the D/A 112. The mass range as well as the duration of the scan can all be preadjusted accordingly. During the mass scan the ions of different masses exiting from the ion source 216 will then be sequentially allowed to pass through the magnetic sector 244 and be detected by the electron multiplier 248. After the mass scan the magnet scan control system 246 automatically returns to the standby condition until a new start scan command signal is received.

As stated previously the start scan command signal is also sent to the CPUII 104 (as an interrupt) to initiate the execution of a mass scan data acquisition program. During this time the A/D 108 and A/D 110 are periodically activated to convert the ion signal detected by the electron multiplier 248, and the magnetic field strength of the magnetic sector 244 (after proper conditioning and amplification), respectively, into digital forms. These trains of digital numbers are then acquired by the CPUII 104, and subsequently stored in the core memory II 116 and the disk storage II 120. The resultant ion intensity vs. magnetic field strength (which is representative of the ion mass) data is then converted (by the data processing programs) to a mass spectrum which is stored in the computer memory and also displayed as seen in the trace 270 through the printed/plotter II 124.

As seen in FIG. 3 in addition to the D/A 112 and CPUII 104, the start scan command signal is also simultaneously sent to the timer 121. This timer 121 can be of any conventional design and can be adjusted such that after a given time delay from the reception of the start scan command signal it will send out a termination command signal to the CPUII 104 (again as an interrupt) to terminate the execution of the mass scan data acquisition program. The duration of this time delay can be normally set to equal to one mass scan cycle in order to assure that one mass scan cycle data is acquired for each GC peak.

The above described operation thus constitutes a SIM (or TIC)—synchronized mass spectrum operation. This operation method, while in the same spirit as the one described previously and exemplified by FIG. 1, provides several new advantages not discussed previously. The most important one of these new advantages is the achievement of high resolution mass spectrometer operation with great ease. In prior art it is generally considered difficult, if not impossible, to perform sample analysis through a high resolution GC—high resolution MS—real time computer system as operated in the repetitive mass spectra acquisition operation mode. The difficulties arise largely because of the limitations in: (1) high resolution mass scan speed; (2) mass spectra storage capability and; (3) real time data processing. In conventional double focusing mass spectrometers, the maximum achievable high resolution mass scan speed is in the order of 5 sec per scan cycle. Unfortunately, this speed is too slow for most high resolution GC if the repetitive mass spectra acquisition must be relied upon for the reconstruction of TIC or mass chromatograph trace. The obtainable chromatographic resolution in such a reconstructed trace is too deteriorated to be of significant analytical value. The problems of mass spectra storage and real time processing limitations mainly result from the enormous amount of data that must be acquired, processed and stored for each high resolution mass spectrum file. To successfully process and store all the data acquired under repetitive mass spectra acquisition operation, an extremely large scale computer system must be employed which is generally considered economically unfeasible.

On the other hand, all these three problems can be eliminated or minimized if the high resolution GC-high resolution MS—real time computer system is operated under the SIM (or TIC)—synchronized mass spectrum operation disclosed herein. With the synchronized mass spectrum operation only one mass scan or acquisition and processing of only one mass scan data is required for each GC peak and a 5-sec high resolution mass scan cycle is fully compatible with most high resolution GC which generally yield a GC peak width of 5–10 sec.

As to the spectra storage, it no longer poses any problem with the TIC (or SIM)—synchronized mass spectrum operation. In this invention a much reduced number of high resolution mass spectra data need to be stored. Finally, in the area of real time data processing, the computer program can be devised such that most real time data processing work can be executed during the "off-peak" time when no mass scan is conducted. The data processing can fall behind data acquisition and then catch up again. In this way the only deciding factor for real time data processing is the total number, rather than the distribution of GC peaks on which the mass spectra must be recorded. In the synchronized mass spectrum operation since a much reduced number of mass spectra are to be recorded, the task of real time data processing is easily handled by most conventional computer systems.

The real time computer-controlled peak sensing can also be far more elaborate than that which can be achieved by the use of an oscilloscope. For example, the peak sensing software program can be devised to differentiate the true GC peak from any false peaks which results from noise spikes or drift in the TIC or SIM trace base line. Computer-controlled multiple ion monitoring can also be readily carried out. Such ion monitoring is often more desirable because it can allow the chromatogram of each of the monitored ions to be individually plotted. More freedom in the choice of the peak sensing criteria can also be achieved as illustrated by the following example: The ratio of the natural abundance of $^{35}Cl$ and $^{37}Cl$ is approximately 3:1. In the analysis of chlorine-containing compounds in a sample mixture, the quadrupole mass filter 230 can be alternately tuned to m/e=35 and 37, respectively, for the detection of $^{35}Cl^-$ and $^{37}Cl^-$ ions. A peak sensing program is thus devised in which a synchronized mass scan is conducted only when both of the following criteria are met: (1) The sum of the intensity of m/e=35 ion and m/e=37 ion reaches a predetermined threshold; (2) The ratio of the intensities of m/e=35 ion and m/e=37 ion is 3:1 within a given error limit. In this manner, a very specific analysis of chlorine-containing compounds is assured, because most non-chlorine compounds are unlikely to fulfill the second criteria and thus are discriminated. A simple algorithm can also be devised to eliminate non-chlorine-containing peaks from the chromatogram.

In the SIM (or TIC)—synchronized mass spectrum operation with the PMS system shown in FIG. 3 the quadrupole mass filter 230 is operated under SIM or TIC mode, while the magnetic sector 244 is operated under a synchronized mass spectrum operation mode. It is obvious from the present teaching that should it be desired, the roles of these two mass resolution devices can be reversed such that the magnetic sector 244 can be operated under SIM mode, while the quadrupole mass filter 230 operated under synchronized mass spectrum operation mode. The magnetic sector 244, along with the electric sector 242, is known as a high mass resolution device which is capable of differentiating ions of same nominal m/e values but of different exact mass values. With this sector 244 tuned to one ion of specific mass an even more specific analysis of compounds of interest can be achieved without interference by compounds which yield ions of the same nominal mass as that of the tuned but with different exact mass values. On the other hand, the obtained mass spectrum by the operation of the quadrupole mass filter 230 in synchronization with the onset or appearance of the GC peak will provide a positive identification of the chromatographic peak in question. The quadrupole mass filter 230 is a low mass resolution device and thus is scanned at a much faster rate which is desirable in dealing with the high performance GC columns yielding very narrow GC peaks. The load on the computer real time data processing and mass storage can also be greatly reduced by handling only the low resolution mass spectra data.

In the PMS system of FIG. 3 there are two ion sources (206 and 216) employed for the simultaneous analysis of the introduced sample through SIM (or TIC)—synchronized mass spectrum operation. It is interesting to note that these two ion sources are operated independently of each other and can be of different configuration. One prime reason for this design is that different voltages can be applied to these two ion sources in order to facilitate the optimum operation of the quadrupole mass filter 230 and the double focusing mass resolution device 240. More importantly, this unique design enables the sample ions to be generated under different ionization mechanism within these two ion sources 206 and 216 should it be desired. It is known from prior art that mass spectra derived from different ionization mechanisms are often complementary to each other and greatly facilitate the analysis of the sample in question. For example, CI mass spectrum often contains a large abundance of quasi-molecular ions, valuable in yielding the molecular weight information. On the other hand, an EI mass spectrum often contains several significant fragment ions which provide valuable information pertaining to the molecular structure of the sample. In the present PMS system of FIG. 3 the ion source 206 can therefore be operated under CI mode with a CI reagent gas introduced into the ion source 206 through the inlet 210, while the ion source 216 is operated under EI mode, which does not require a CI reagent gas. The quadrupole mass filter 230 is tuned to the quasi-molecular ion, which is normally in large abundance. The magnetic sector 244 is operated under synchronized mass spectrum operation and provides EI spectra for the structure elucidation of the sample presented in the chromatographic peaks.

It is to be emphasized that the PMS system of FIG. 3 above described is presented here only to serve as an illustration, while in reality many variations or simplifications can be realized within the teaching of the present invention. For example, the CPUI 102 and CPUII 104 can be integrated into one central processing unit. All the peripheral devices can also be consolidated for cost saving. The timer 121 can be eliminated if the timing can be internally controlled within the CPUII 104.

Many other examples of the variations or simplifications can also be cited. Discussed in the following are two more such examples, which although differs in some details from what was described, are well within the teaching of the present invention. For the first example, the start command signal in FIG. 3 is shown sent to the D/A 112, CPUII 104 and timer 121. It is obvious that as long as the initiation and termination of the mass scan data acquisition operation of the CPUII is under the control of the start scan command signal, the magnet scan control system 246 needs not be redundantly also under the control of the stard scan command signal. For example, the magnet scan control system 246 can be operated in the conventional repetitive mass scanning mode which would allow the elimination of the D/A 112. In this case the mass scan data are acquired still only during the appearance of a GC peak (as controlled by the start scan command signal) in spite of the fact that ion signals are continuously detected by the electron multiplier 248. The only complication is that the acquired mass spectrum data may be actually obtained during the tail portion of one mass scan cycle and the leading portion of the next mass scan cycle. But this complication can be easily resolved by the CPUII 104 in providing a true mass spectrum in synchronization with the appearance of each GC peak.

The second example to be discussed here concerns the fact that although the acquisition of one mass spectrum in synchronization with the appearance of a GC peak is desirable, several background mass spectra during a typical GC run are also needed for correction of the acquired mass spectra due to background ion signals which inevitably exist in most mass spectrometer systems. One possible approach which is again basically according to the PMS system of FIG. 3 and within the teaching of the present invention can be cited for solving this background subtraction task. Under this approach the magnet scan control system 246 is operated in the repetitive mass scanning mode with the detected ion signals (raw data) continuously digitized and stored in a temporary memory location. However, among all these stored raw data only the portion collected in synchronization with the appearance of th GC peak is signaled by the start scan command will be utilized and processed to yield the mass spectra. In this case the CPUI 102 must be programmed to guide (to tell) the CPUII 104 not only which portion of the stored raw data are collected in synchronization with the appearance of a GC peak and must be selected and processed to yield the mass spectrum but also to tell the CPUII 104 what portion of the stored raw data are collected when the GC trace (i.e. 260) is at its base line and can be utilized and processed to yield a background mass spectrum. Once all these data processings are completed and the background-corrected mass spectrum in synchronization with the appearance of a GC peak is obtained, the raw data stored in the temporary memory location can then be erased which makes the same location ready to store the next batch of raw data. It is clear that in spite of the complication in this example the basical underline principle of SIM (or TIC)—synchronized mass spectrum operation is still the same as previously described in which a mass spectrum (except that it will undergo a background correction procedure) is acquired in synchronization with the appearance of a chromatographic peak as automatically controlled by the peak sensor (CPUI 102).

In regard to any scanning mass spectrometer, it is well known that the recorded mass spectrum is distorted if the sample stream is not introduced into the mass spectrometer continuously at a constant flow rate during the scanning period.

Mass spectrum distortion occurs when a mass spectrometer is used to analyze a sample introduced from a gas chromatograph. This distortion cannot be accurately corrected in the prior art operation because one does not know how the sample concentration is changing during the mass scan.

On the other hand, in the chemical analysis method of the present invention, a chromatogram, either total ion current (TIC) or select ion monitoring (SIM) is recorded separately and independently from the mass scan operation. The profile of the chromatograph peak reveals exactly how the sample concentration is changing during the mass scan, and thus provides a basis for mass spectrum correction.

As stated the simplest mass spectrum correction routine is to divide the intensity of each ion in the recorded MS trace by the corresponding height shown in the TIC or SIM trace and followed with proper normalization process.

For the sake of clarity, the above stated correction routine is executed using the data shown in FIG. 2 as an example. The ion mass spectrum trace in the figure shows four ions recorded at the time of 52, 53, 55, and 56 seconds, respectively. The intensities of these ions (measured in centimeters,) are 1.4, 0.9, 2.3, and 1.8, respectively. However, this mass spectrum does not represent the true mass spectrum of the sample, because during the mass scan the sample concentration changes continuously as represented by the TIC trace. This TIC trace indicates that the sample concentration when the four ions are recorded are multiples of 0.9, 1.6, 2.8, and 2.4, respectively. The above four numbers are simply the heights of the TIC trace (measured in centimeters,) at the time of 52, 53, 55, and 56 seconds, respectively. According to the correction instruction, the concentration-corrected mass spectrum should therefore contain the four ions with their relative ion intensities of 1.56 (1.4/0.9), 0.56 (0.9/1.6), 0.82 (2.3/2.8), and 0.75 (1.8/2.4), respectively. The procedure of normalization is merely to rewrite the mass spectrum in the conventional format in which the highest ion intensity is assigned with an arbitrary number of 100. The final spectrum thus consists of four ions with their relative intensities of 100, 36 (0.56/1.56×100), 52 (0.82/1.56×100), and 48 (0.77/1.56×100), respectively.

It is clear from the above illustration that the concentration-corrected mass spectrum (trace 56) is obtained based on the TIC trace and the ion mass spectrum (trace 52) exactly following the instruction stated in the text. This corrected mass spectrum is the accurate mass spectrum which would be obtained directly without any correction if the sample were introduced continuously at a constant flow rate. This correction procedure, although new in the mass spectrometry, is based on a sound mathematical principle.

Although the preferred embodiment of the parallel mass spectrometer of this invention has been described, it will be understood that within the purview of this invention various changes may be made in the form, details, proportion and arrangement of parts, the combination thereof, and the mode of operation, which generally stated consist in an invention within the scope of the appended claims.

The invention having thus been described, the following is claimed:

1. A chromatograph-mass spectrometer chemical analysis method including the following steps during a chromatograph-mass spectrometer experiment:
  A. transmitting a sample from a chromatograph into a mass spectrometer equipped with ion generation means, ion direction means, a first mass resolution device, a second mass resolution device, ion detection means and operation means,
  B. generating ions of the sample in the mass spectrometer,
  C. simultaneously and separately directing a first portion of the ions into the first mass resolution device and directing a second portion of the ions into the second mass resolution device,
  D. operating the first mass resolution device for obtaining a chromatogram,
  E. detecting the ions emerging from the first mass resolution device and yielding a first output signal,
  F. automatically sensing the time during which the first output signal corresponds to the appearance of a chromatographic peak,
  G. operating the second mass resolution device and detecting the ions emerging from the second mass resolution device, which yields a second output signal and producing a mass spectrum from the second output signal,
  H. automatically controlling at least a portion of the Step G operation in accordance with the time information sensed.

2. The chemical analysis method of claim 1 in which the Step B includes generating ions of the sample in the mass spectrometer under electron impact ionization.

3. The chemical analysis method of claim 1 in which the Step B includes generating ions of the sample in the mass spectrometer under chemical ionization.

4. The chemical analysis method of claim 1 in which:
  the Step B includes generating ions of both positive charge and negative charge of the sample in the mass spectrometer,
  the Step C includes simultaneously and separately directing a first portion of the ions and a second portion of the ions, with charges opposite to each other, into the first mass resolution device, and the second mass resolution device, respectively.

5. The chemical analysis method of claim 1 in which the Step B includes generating ions of the sample in a first ionization region and in a second ionization region of the mass spectrometer, separately and simultaneously.

6. The chemical analysis method of claim 5 in which the Step B includes generating ions of the sample in the first ionization region under electron impact ionization and in the second ionization region under chemical ionization.

7. The chemical analysis of claim 1 in which:
  the Step D includes operating the first mass resolution device under fast repetitive mass scan operation, and
  the Step E includes integrating the first output signal for obtaining a total ion current chromatogram.

8. The chamical analysis method of claim 1 in which the Step D includes operating the first mass resolution device under high pass filtering mode (or commonly called RF-only mode) for obtaining a total ion current chromatogram.

9. The chemical analysis method of claim 1 in which the Step D includes operating the first mass resolution device under select ion monitoring mode for obtaining a select ion monitoring chromatogram.

10. The chemical analysis method of claim 9 in which the Step D includes operating the first mass resolution device under single ion monitoring mode for obtaining a single ion monitoring chromatogram.

11. The chemical analysis method of claim 9 in which the Step D includes operating the first mass resolution device under multiple ion monitoring mode for obtaining a multiple ion monitoring chromatogram.

12. The chemical analysis method of claim 1 in which the Step H includes automatically controlling the Step G operation by sending out a command signal in synchronization with said time.

13. The chemical analysis method of claim 1 in which the Step G includes producing a mass spectrum by initiating a mass scan operation of the second mass resolution device during said time.

14. The chemical analysis method of claim 1 in which:
  the Step G includes producing a mass spectrum based on the second output signal obtained in substantial synchronization with said time.

15. The chemical analysis method of claim 1 in which the Step G includes producing the mass spectrum in analog form.

16. A mass spectrometer capable of interfacing with a chromatographic separation device for carrying out a chromatograph-mass spectrometer experiment, comprising:
  sample receiving means for receiving a sample from the chromatographic separation device for sample analysis,
  ion generation means for generating ions characteristic of the introduced sample,
  ion extraction means for extracting at least some of the generated ions and forming said ions into a first ion beam and a second ion beam,
  first mass resolution means for resolving said first ion beam according to the ion-mass-to-charge ratio,
  second mass resolution means for resolving said second ion beam according to the ion-mass-to-charge ratio,
  first detector means located at the exit of the first mass resolution means for detecting the first ion beam and yielding a first detector output signal,
  second detector means located at the exit of the second mass resolution means for detecting the second ion beam and yielding a second detector output signal, and operation means for automatically executing the following steps during the chromatograph-mass spectrometer experiment:
A. operating the first mass resolution means for obtaining a chromatogram,
B. sensing the time during which the first detector output signal corresponds to the appearance of a chromatographic peak,
C. operating the second mass resolution means and the second detector means, and producing a mass spectrum from the second detector output signal,
D. and controlling at least a portion of the Step C operation in accordance with the time information sensed.

17. The mass spectrometer of claim 1 in which the ion generation means includes ion source means forming an ionization region.

18. The mass spectrometer of claim 1 in which the ion generation means includes a first ion source means forming a first ionization region and a second ion source means forming a second ionization region.

19. The mass spectrometer of claim 18 in which the ion generation means includes means for generating ions within the first ion source means under electron impact ionization and in which said ion generation means also includes means for generating ions within the second ion source means under chemical ionization.

20. The mass spectrometer of claim 1 in which the ion generation means includes means for generating ions under electron impact ionization.

21. The mass spectrometer of claim 1 in which the ion generation means includes means for generating ions under chemical ionization.

22. The mass spectrometer of claim 1 in which:
the ion generation means includes means for generating ions of positive and negative charge polarities, and
the ion extraction means includes means for forming the extracted ions into a first ion beam and a second ion beam of opposite charges.

23. The mass spectrometer of claim 1 in which the first mass resolution means and the second mass resolution means are of quadrupole type.

24. The mass spectrometer of claim 1 in which the first mass resolution means is of quadrupole type, and the second mass resolution means is of magnetic sector type.

25. The mass spectrometer of claim 1 in which the first mass resolution means is of magnetic sector type, and the second mass resolution means is of quadrupole type.

26. The mass spectrometer of claim 1 in which the operation means includes:
means for operating the first mass resolution means in repetitive fast mass scanning mode,
and signal integration means for integrating the first detector output signal for obtaining a total ion current chromatogram.

27. The mass spectrometer of claim 1 in which
the first mass resolution means is of quadrupole type,
the operation means includes means for operating the first mass resolution means in high pass filter mode (RF-only mode) for obtaining a total ion current chromatogram.

28. The mass spectrometer of claim 1 in which the operation means includes means for operating the first mass resolution means in select ion monitoring mode for obtaining a select ion monitoring chromatogram.

29. The mass spectrometer of claim 28 in which the select ion monitoring mode is a single ion monitoring mode,
and the select ion monitoring chromatogram is a single ion monitoring chromatogram.

30. The mass spectrometer of claim 28 in which the select ion monitoring mode is a multiple ion monitoring mode,
and the select ion monitoring chromatogram is a multiple ion monitoring chromatogram.

31. The mass spectrometer of claim 1 in which the operation means includes oscilloscope means for the operation of Step B.

32. The mass spectrometer of claim 1 in which the operation means includes computer means for the operation of Steps B, C and D.

33. The mass spectrometer of claim 1 in which the operation means includes digital signal-to-analog signal converting means.

34. A chromatograph-mass spectrometer chemical analysis method including the following steps during a chromatograph-mass spectrometer experiment:
A. transmitting a sample from a chromatograph into a mass spectrometer equipped with ion generation means, ion direction means, a first mass resolution device, a second mass resolution device, ion detection means, and operation means,
B. generating ions of the sample in the mass spectrometer,
C. separately directing a first portion of the ions into the first mass resolution device and directing a second portion of the ions into the second mass resolution device,
D. operating the first mass resolution device,
E. operating the second mass resolution device and detecting the ions emerging therefrom, and producing a mass spectrum from the detected ions,
F. and detecting the ions emerging from the first mass resolution device which yields a first output signal for automatically controlling at least a portion of the Step E.

35. The chemical analysis method of claim 34 in which the Step B includes generating ions of the sample in the mass spectrometer under electron impact ionization.

36. The chemical analysis method of claim 34 in which the Step B includes generating ions of the sample in the mass spectrometer under chemical ionization.

37. The chemical analysis method of claim 34 in which:
the Step B includes generating ions of both positive charge and negative charge in the mass spectrometer, and
the Step C includes separately directing a first portion of the ions and a second portion of the ions, with charge opposite to each other, into the first mass resolution device and the second mass resolution device, respectively.

38. The chemical analysis method of claim 34 in which the Step D includes operating the first mass resolution device under total ion current mode for obtaining a total ion current chromatogram.

39. The chemical analysis method of claim 34 in which the Step D includes operating the first mass resolution device under select ion monitoring mode for obtaining a select ion monitoring chromatogram.

40. The chemical analysis method of claim 34 in which the Step E includes initiating a mass scan operation of the second mass resolution device for producing a mass spectrum.

41. The chemical analysis method of claim 1 in which the step G includes producing the mass spectrum in digital form.

42. The chemical analysis method of claim 1 further including the step:
 I. correcting said mass spectrum for fluctuations of the sample concentration in the mass spectrometer in accordance with said chromatogram.

* * * * *

UNITED STATES PATENT AND TRADEMARK OFFICE
CERTIFICATE OF CORRECTION

PATENT NO. : 4,507,555
DATED : March 26, 1985
INVENTOR(S) : Cherng Chang

It is certified that error appears in the above-identified patent and that said Letters Patent are hereby corrected as shown below:

```
Title Page (76) INVENTORS NAME, change "Chang" to ---Cherng---

Column 15, line 59, change "is" to ---as---.
Column 16, line 65, change "(0.77" to ---(0.75---.
Column 19, line 15, change "1" to ---16---.
Column 19, line 18, change "1" to ---16---.
Column 19, line 28, change "1" to ---16---.
Column 19, line 31, change "1" to ---16---.
Column 19, line 34, change "1" to ---16---.
Column 19, line 41, change "1" to ---16---.
Column 19, line 44, change "1" to ---16---.
Column 19, line 48, change "1" to ---16---.
Column 19, line 52, change "1" to ---16---.
Column 19, line 59, change "1" to ---16---.
Column 19, line 65, change "1" to ---16---.
Column 20, line 11, change "1" to ---16---.
Column 20, line 14, change "1" to ---16---.
Column 20, line 17, change "1" to ---16---.
```

Signed and Sealed this

Tenth Day of September 1985

[SEAL]

Attest:

DONALD J. QUIGG

Attesting Officer    Acting Commissioner of Patents and Trademarks - Designate